(12) United States Patent
Guntinas-Lichius et al.

(10) Patent No.: US 8,792,989 B2
(45) Date of Patent: Jul. 29, 2014

(54) SYSTEM AND METHOD FOR FACIAL NERVE STIMULATION

(75) Inventors: Orlando Guntinas-Lichius, Jena (DE); Andreas Müller, Gera (DE); Werner Lindenthaler, Oberperfuss (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 333 days.

(21) Appl. No.: 12/582,990

(22) Filed: Oct. 21, 2009

(65) Prior Publication Data
US 2010/0114240 A1 May 6, 2010

Related U.S. Application Data

(60) Provisional application No. 61/107,081, filed on Oct. 21, 2008.

(51) Int. Cl.
*A61N 1/18* (2006.01)

(52) U.S. Cl.
USPC ............... 607/48; 607/50; 607/116; 607/117; 607/118

(58) Field of Classification Search
CPC ...... A61N 1/056; A61N 1/36003; A61N 1/36
USPC ..................... 607/45–50, 116–118
See application file for complete search history.

(56) References Cited

U.S. PATENT DOCUMENTS

| | | | |
|---|---|---|---|
| 3,279,468 A | 10/1966 | Le Vine | |
| 3,851,651 A | 12/1974 | Icenbice | |
| 4,165,750 A | 8/1979 | Aleev et al. | |
| 5,350,414 A | 9/1994 | Kolen | |
| 5,772,605 A * | 6/1998 | Weijand | 600/547 |

(Continued)

FOREIGN PATENT DOCUMENTS

| | | |
|---|---|---|
| FR | 2279376 A1 | 2/1976 |
| WO | 03020363 A1 | 3/2003 |
| WO | 2005062829 A2 | 7/2005 |
| WO | 2008097407 A2 | 8/2008 |

OTHER PUBLICATIONS

International Search Report and Written Opinion of the International Searching Authority, International Application No. PCT/US2009/061441, dated Dec. 24, 2009 (10 pages).

(Continued)

*Primary Examiner* — Joseph Stoklosa
(74) *Attorney, Agent, or Firm* — Sunstein Kann Murphy & Timbers LLP

(57) ABSTRACT

A method for stimulating facial nerves in a subject with synkinetic reinnervated muscles includes providing an electrode, having a plurality of contacts, in a parotic region of the subject's face, stimulating each of the contacts separately, identifying one or more contacts from the plurality of contacts that cause one or more nerve branches to activate a desired facial muscle, and selecting the identified contacts to stimulate the one or more nerve branches. The system includes an electrode having a plurality of contacts for placement in a parotic region of the subject's face and a processor in communication with the electrode. The processor has program code for stimulating each of the contacts separately, for identifying one or more contacts from the plurality of contacts that cause one or more nerve branches to activate a desired facial muscle, and for selecting the identified contacts to stimulate the one or more nerve branches.

18 Claims, 11 Drawing Sheets

(56) References Cited

U.S. PATENT DOCUMENTS

| | | | |
|---|---|---|---|
| 6,233,472 B1* | 5/2001 | Bennett et al. | 600/383 |
| 6,516,227 B1* | 2/2003 | Meadows et al. | 607/46 |
| 6,892,098 B2* | 5/2005 | Ayal et al. | 607/48 |
| 7,774,068 B1* | 8/2010 | Lozano | 607/48 |
| 2003/0055468 A1 | 3/2003 | Sachs | |
| 2005/0222626 A1 | 10/2005 | DiLorenzo | |
| 2007/0088335 A1 | 4/2007 | Jolly | |
| 2008/0147141 A1 | 6/2008 | Testerman et al. | |

OTHER PUBLICATIONS

Angelov et al., "Axonal Branching and Recovery of Coordinated Muscle Activity after Transection of the Facial Nerve in Adult Rats", Adv. Anat. Embryol. Cell Bio., vol. 180, pp. 1-130 (2005).

Broniatowski et al., "An Experimental Model for Complex Dynamic Control of the Reinnervated Face", Eur. Arch. Otorhinolaryngol. (Supp.), pp. S147-S148 (1994).

Broniatowski et al., "Dynamic rehabilitation of the paralyzed face: I. Electronic control of reinnervated muscles from intact facial musculature in the rabbit", Otolaryngol.—Head Neck Surg., vol. 97, No. 5, pp. 441-445 (1987).

Broniatowski et al., "Dynamic rehabilitation of the paralyzed face—II. Electronic control of the reinnervated facial musculature from the contralateral side in the rabbit", Otolaryngol.—Head Neck Surg., vol. 101, No. 3, pp. 309-313 (1989).

Broniatowski et al., "Dynamic rehabilitation of the paralyzed face: III: Balanced coupling of oral and ocular musculature from the intact side in the canine", Otolaryngol.—Head Neck Surg., vol. 105, No. 5, 727-733 (1991).

Guntinas-Lichius, "The facial nerve in the presence of a head and neck neoplasm: assessment and outcome after surgical management", Curr. Opin. Otolaryngol. Head Neck Surg., vol. 12, pp. 133-141 (2004).

Guntinas-Lichius et al., "Diagnostics of diseases and the function of the facial nerve", HNO, vol. 15, pp. 1115-1131 (2004).

Guntinas-Lichius et al., "Factors limiting motor recovery after facial nerve transection in the rat: combined structural and functional analyses", Eur. J. Neurosci., vol. 21, pp. 391-402 (2005).

Moran et al., "Patterns of Facial Nerve Synkinesis", The Laryngoscope, vol. 106, pp. 1491-1496 (1996).

Nicolaidis et al., "Muscle Preservation Using an Implantable Electrical System After Nerve Injury and Repair", Microsurgery, vol. 21, pp. 241-247 (2001).

Otto, "Restoration of Function in the Paralyzed Rabbit Orbicularis Oculi Muscle by Direct Functional Electrical Stimulation", The Laryngoscope, vol. 107, pp. 101-111 (1997).

Peckham et al., "Functional Electrical Stimulation for Neuromuscular Applications", Annu. Rev. Biomed. Eng., vol. 7, pp. 327-360 (2005).

Rothstein et al., "Electronic reanimation of facial paralysis—A feasibility study", Otolaryngol. Head Neck Surg., vol. 94, No. 1, pp. 82-85 (1986).

Scholle et al., "A surface EMG multi-electrode technique for characterizing muscle activation patterns in mice during treadmill locomotion", J. Neurosci. Methods, vol. 146, pp. 174-182 (2005).

Somia et al., "Multi-Channel Orbicularis Oculi Stimulation to Restore Eye-Blink Function in Facial Paralysis", Microsurgery, vol. 21, pp. 264-270 (2001).

Stennert, "The Autoparalytic Syndrome—A Leading Symptom of Postparetic Facial Function", Arch. Otorhinolaryngol., vol. 236, pp. 97-114 (1982).

Zealear et al., "Control of Paralysed Axial Muscles by Electrical Stimulation", Acta Otolaryngol., vol. 83, pp. 514-527 (1977).

Zealear et al., "Electrical Pacing of the Paralyzed Human Larynx", Ann. Otol. Rhino. Laryngol., vol. 105, pp. 689-693 (1996).

Zealear et al., "Determination of the optimal conditions for laryngeal pacing with the Itrel II implantable stimulator", Otolaryngol.—Head Neck Surg., vol. 125, No. 3, pp. 183-192 (2001).

Zealear et al., "Reanimation of the Paralyzed Human Larynx With an Implantable Electrical Stimulation Device", The Laryngoscope, vol. 113, pp. 1149-1156 (2003).

Zeng, "Trends in Cochlear Implants", Trends Amplif., vol. 8, No. 1, pp. 1-34 (2004).

Supplementary European Search Report for European Patent Application No. 09 822 609.5 dated Apr. 11, 2012, 5 pages.

\* cited by examiner

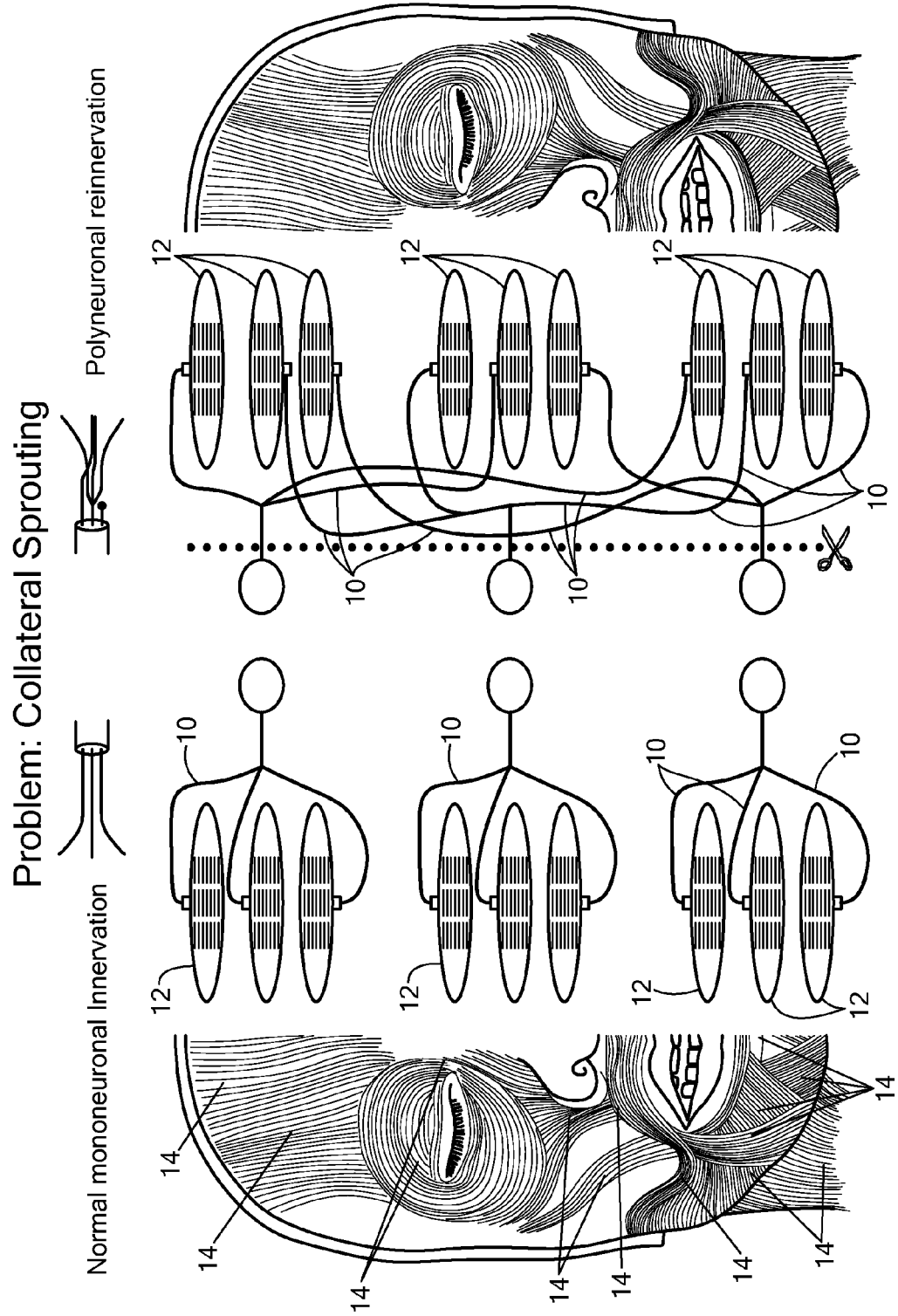

SYSTEM AND METHOD FOR FACIAL NERVE STIMULATION

CROSS REFERENCE TO RELATED APPLICATIONS

The present application claims priority to U.S. Provisional Patent Application No. 61/107,081 filed Oct. 21, 2008, the disclosure of which is incorporated by reference herein in its entirety.

FIELD OF THE INVENTION

The invention generally relates to stimulation systems and, more particularly, the invention relates to facial nerve stimulation.

BACKGROUND OF THE INVENTION

The face is the mirror of the soul and facial expressions are an indispensable element of verbal and nonverbal human communication. Degenerative lesions of the facial nerve, such as tumors or traumas, lead to permanent facial nerve damage which, in contrast to many other neural lesions, cannot be hidden. Functional rehabilitation of facial nerve paresis has remained unsatisfactory despite optimal microsurgical reconstruction of the damaged nerve parts.

Unilateral damage of the nerve fibers of the facial nerve or its nucleus leads to peripheral facial paresis. This is to be distinguished from supranuclear lesions along the cortico-nuclear tract which lead to a so-called central facial paresis. In Western Europe and the USA, the incidence of peripheral facial pareses is approx. 20-35/100,000 inhabitants. The most frequent reasons for peripheral facial paresis are idiopathic facial paresis (two thirds of the cases, no reason can be found despite extensive diagnostics), traumatic pareses following fractures of the petrous part of the temporal bone or face injuries, inflammatory paresis accompanying chronic ear infections, and destruction of the nerve by tumors. The incidence of central facial pareses is 200/1,000,000 inhabitants, as the incidence of the most frequent cause of central facial paresis, i.e., stroke which often causes facial paresis, is 250/100,000 inhabitants. Cerebral hemorrhage, cerebral inflammation and brain tumors are less frequent causes of the central form.

Thus, facial paresis is a common disease. In most cases and depending on the cause, peripheral paresis shows non-degenerative paresis (neurapraxia according to Seddon) so that 80% of the cases show regeneration of the nerve under adequate therapy. 95% of cases with central facial paresis show regeneration. In cases of degenerative paresis (axonotmesis, neurotmesis, mixed forms according to Seddon) caused by the destruction of nerve fibers, persistent defects are observed after healing. The extent of persistent defects after healing depends on the degree of the neural lesion and the applied therapy. If only a small peripheral branch of the facial nerve is affected, mimic muscles only show very localized deficits. A complete loss of the peripheral facial nerve leads to a loss of muscle tone in the affected half of the face and the soft tissues of the face sag. Voluntary motor movement is lost, and mimic muscles can no longer be moved. The inability to close the eyelid indirectly leads to vision disorders since the eye waters and inflammation is possible. Lack of mouth movement limits speaking and eating.

In our modern society, facial expression is the essential factor of verbal and nonverbal communication. As opposed to other pareses, facial paresis cannot be hidden. Patients feel stigmatized, and often retreat from the public and develop secondary psychical disorders, e.g., depressions. The patients' quality of life is significantly curbed. Persistent defects after healing are even observed in cases of spontaneous regeneration or optimal and extensive surgical reconstruction of the nerve in cases of nerve transsection and bridging of the defect with neural transplants. Sprouting of the regenerating axons is observed at the site of the lesion even after reconstruction of nerve continuity. At the same time, Wallerian degeneration of the entire affected section of the nerve as far as the muscles is completed until only the Bungner's bands remain as Schwann cell conducting structures. The regenerating neurons with their sprouting axons grow accidentally into these bands of the individual nerve branches and are directed to the peripheral mimic muscles. Individual axons perish and do not reach the periphery, some accidentally reach their original target muscle, while others reach a completely different target muscle. Due to axonal collateral sprouting, the most frequently observed effect is simultaneous sprouting to several target muscles, such as shown in FIGS. 1A and 1B.

This leads clinically to simultaneous movement of several target muscles (a condition called synkinesis). Patients often complain about involuntary lid closure while moving the mouth, e.g., when eating. Simultaneous movement of antagonist muscles leads to the autoparalytic syndrome: muscle forces cancel each other out and no movement is observed clinically despite innervation. New research shows that not only collateral sprouting but also terminal sprouting (such as shown in FIGS. 2A and 2B) of the regenerating axons directly at the neuromuscular end-plates causes uncoordinated muscle function. This explains why the patients' quality of life is significantly limited even after surgical reconstruction of the nerve. If the lesion is so extensive that the remaining peripheral part of the facial nerve is insufficient, or if Bungner's bands are fibrosed due to failed reinnervation and muscles are atrophied due to long-term denervation of more than 3 to 5 years, the patient can no longer be offered a nerve graft.

Possible therapies include dynamic muscle grafts, free nerve-muscle transplantation, implantation of upper lid weights or static suspensions. Functional results of these secondary procedures are even less satisfactory than the above mentioned nerve grafts. These procedures may, at best, restore muscle tone, but facial expression remains very mask-like and the dynamic muscle suspensions allow reproducing only few and very mechanistic movement vectors.

SUMMARY OF THE INVENTION

In accordance with one embodiment of the invention, a method of stimulating facial nerves in a subject with synkinetic reinnervated muscles includes providing an electrode, having a plurality of contacts, in a parotic region of the subject's face. The method also includes stimulating each of the plurality of contacts separately, identifying one or more contacts from the plurality of contacts that cause one or more nerve branches to activate a desired facial muscle, and selecting the identified contacts to stimulate the one or more nerve branches.

In accordance with related embodiments, the electrode may be an array electrode and/or a rod electrode. The facial muscle may be the orbicularis oculi muscle, the orbicularis oris muscle, the occipitofrontalis muscle, the procerus muscle, the nasalis muscle, the depressor septi nasi muscle, the corrugator supercilii muscle, the depressor supercilii muscle, the auricular muscles (anterior, superior, posterior), the depressor anguli oris muscle, the risorius muscle, the zygomaticus major muscle, the zygomaticus minor muscle, the levator labii superioris muscle, the levator labii superioris alaeque nasi muscle, the depressor labii inferioris muscle, the levator anguli oris muscle, the buccinator muscle, and/or the mentalis muscle. The electrode may be implanted within an operable distance of the one or more nerve branches, e.g., implanted below one or more nerve branches or implanted above the nerve branches between the nerve branches and the subject's skin. The stimulation of the one or more nerve branches may be triggered based on a sensed signal, e.g., measured using EMG sensors and/or acceleration sensors. The sensed signal may be recorded from a recording electrode in the parotic region of the subject's damaged side and/or healthy side of the face. The recording electrode may have a plurality of contacts. The sensed signal may be recorded from sensors placed on or under the subject's skin. The method may further include selecting one or more contacts to stimulate nerve branches in order to block activation of other facial muscles. The method may identify one or more first contacts that cause the activation of a first facial muscle and one or more second contacts that cause the activation of a second facial muscle. The method may then select the identified first and second contacts.

In accordance with another embodiment of the invention, a system for stimulating facial nerves in a subject includes an electrode having a plurality of contacts and a processor in communication with the electrode. The processor has program code for stimulating each of the plurality of contacts separately, for identifying one or more contacts from the plurality of contacts that cause one or more nerve branches to activate a desired facial muscle, and for selecting the identified contacts to stimulate the one or more nerve branches.

In accordance with related embodiments, the electrode may be an array electrode and/or a rod electrode. The system may further include one or more sensors in communication with the processor. The sensors may be configured to provide facial movement information to the processor for use with the program code for identifying one or more contacts. The sensors may be EMG sensors and/or acceleration sensors. The program code for selecting the identified contacts may continuously stimulate the one or more nerve branches to maintain or recover a damaged side of a hemiparalyzed face.

In accordance with another embodiment of the invention, a method of stimulating facial nerves in a subject with facial palsy includes providing an electrode, having a plurality of contacts, in a parotic region of the subject's face. The method also includes stimulating each of the plurality of contacts separately, identifying one or more contacts from the plurality of contacts that cause one or more nerve branches to activate a desired facial muscle, and selecting the identified contacts to continuously stimulate the one or more nerve branches.

In accordance with related embodiments, the electrode may be an array electrode and/or a rod electrode. The electrode may be implanted within an operable distance of the one or more nerve branches, e.g., implanted below one or more nerve branches or implanted above the nerve branches between the nerve branches and the subject's skin. The stimulation of the one or more nerve branches may be triggered based on a sensed signal, e.g., measured using EMG sensors and/or acceleration sensors. The recording electrode may have a plurality of contacts. The sensed signal may be recorded from sensors placed on or under the subject's skin. The method may identify one or more first contacts that cause the activation of a first facial muscle and one or more second contacts that cause the activation of a second facial muscle. The method may then select the identified first and second contacts.

BRIEF DESCRIPTION OF THE DRAWINGS

The foregoing advantages of the invention will be appreciated more fully from the following further description thereof with reference to the accompanying drawings wherein:

FIG. 1A shows a diagram of normal somatotopic organization of facial innervation and FIG. 1B shows the condition after lesion of the facial nerve;

DESCRIPTION OF ILLUSTRATIVE EMBODIMENTS

Figure 2A:
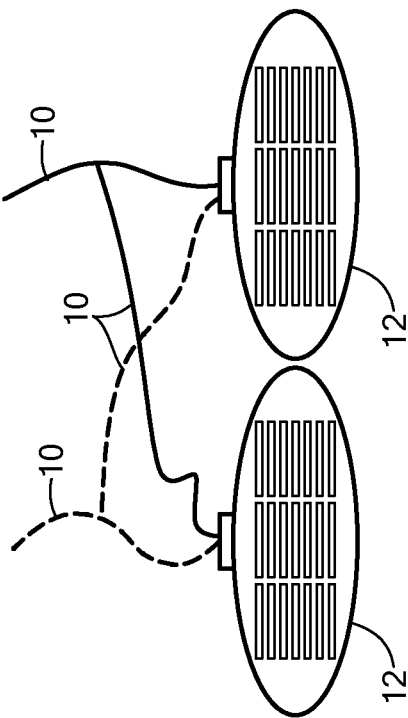
FIG. 2A shows a diagram of a normal end-plate region on a muscle fiber and FIG. 2B shows a diagram of end-plates activated by several axons due to terminal sprouting.

Various embodiments of the present invention provide a neuroprosthesis for restoring or partially restoring a unilaterally paralyzed face. The muscle(s) of interest for rehabilitation are synkinetic (i.e., misdirected) reinnervated muscles and not denervated muscles. Embodiments apply electrostimulation in a prescribed manner and location in order to stimulate the appropriate facial nerves on the damaged side of a subject's face. This is accomplished by placing an electrode in the parotic region of the subject's damaged side of the face and stimulating the appropriate nerve branches in order to activate the desired facial muscles. The sum action potential of the activated mimic muscles may be recorded with a medical device, such as an EMG and/or acceleration sensor. This impulse may then be used to determine which nerves branches to subsequently stimulate in order to activate the desired mimic muscles on the damaged side of the face. This potentially allows the facial muscles of both the healthy side and the corresponding damaged side to move synchronously. Details of illustrative embodiments are discussed below.

The detailed description lists several embodiments of the presently disclosed subject matter, and in many cases lists variations and permutations of these embodiments. This description is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed herein or not. To avoid excessive repetition, this description does not list or suggest all possible combinations of such features.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a muscle" {e.g., "a PCA muscle") includes a plurality of such muscles (e.g., a plurality of PCA muscles), and so forth.

Unless otherwise indicated, all numbers expressing quantities of ingredients, reaction conditions, electrical measurements and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, quantity, volume, current, concentration or percentage is meant to encompass variations of in some embodiments +/−20%, in some embodiments +/−10%, in some embodiments +/−5%, in some embodiments +/−1%, in some embodiments +/−0.5%, and in some embodiments +/−0.1% from the specified value, as such variations are appropriate.

The terms "subject" and "patient" are used interchangeably herein and each term refers, preferably, to a vertebrate subject or patient. A representative vertebrate is warm-blooded; a representative warm-blooded vertebrate is a mammal. A representative mammal is a human. As used herein, the terms "subject" and "patient" include both human and animal subjects. Thus, veterinary therapeutic uses are provided in accordance with the presently disclosed subject matter. As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, e.g., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses and show horses), poultry, and the like.

Based on the works of Zealear and Dedo (1977), who were the first to succeed in stimulating paralyzed laryngeal muscles of dog by electrically stimulating the contralateral side, Rothstein and Berlinger developed the idea of electrical reanimation of the paralyzed face through the contralateral healthy side in 1986. They were the first to succeed in stimulating facial muscles of rabbit with implanted steel electrodes and elicit facial movements after two weeks of denervation. The group did not perform any further investigations. After a denervation interval of two weeks, the orbicularis oculi muscle of dog is also stimulated with successful eyelid closure using 8-channel electrodes. This was not possible with a 1-channel electrode. In rabbit, eyelid closure could be re-established with two 1-channel electrodes (from a cardiac pacemaker) in the upper and lower lid following 30 days of electrostimulation of the freshly denervated orbicularis oculi muscle. The work group of Broniatowski used a different approach, neurotization. Unilaterally denervated infrahyoidal muscles of rabbit (originally innervated by the hypoglossal nerve) were reinnervated by a neuromuscular transplant of the contralateral side sutured to the denervated muscles. Twenty weeks later, a compression electrode was inserted into the healthy facial muscles.

Facial movements led to compression of the electrodes and thus to stimulation. The signal was externally amplified and the stimulation electrode stimulated. The stimulation electrode was placed around the neural stump of the neuromuscular transplant as a cuff electrode. Facial movements of rabbit led to contraction of the originally denervated neck muscles. In a second step, the same technique principally enabled electrostimulation of the denervated orbicularis oculi muscle of rabbit using the signal of the same muscle of the healthy side. The publication does not detail recording and stimulation parameters. Also, the duration of the experiment remains unclear. Cadaver examinations showed that the same neuromuscular transplants can be used for neurotization in the human face. The experiment was repeated one last time in dog. For the first time, parallel recordings and associated stimulations were done simultaneously from two muscles, the orbicularis oculi and oris muscles. Additional continuous stimulation was also used for the first time to copy muscle tone. A limiting factor should be mentioned, i.e., that the muscle movements on the healthy side did not result from normal voluntary activity of the animal but from direct electrostimulation of the exposed facial nerve of the healthy side of the anesthetized animal. Long-term experiments were not performed.

To prevent atrophy of the denervated facial muscles, three patients whose nerve had been reconstructed with a nerve graft were temporarily stimulated with an implanted pulse generator (Medtronic Implantable Pulse Generator®, IPG), embedded into a supraclavicular pouch. The stimulation electrodes were periorbitally, nasally and periorally embedded in the muscle. Complications did not occur. One implant remained in the body for 304 days. There is no information on the other two implants, stimulation parameters are not given. The functional results are not described. The workgroup has not published any more articles.

In another area of ENT medicine, i.e., laryngology, research on electrostimulation in cases of vocal cord paresis is far more advanced than on applications in cases of facial nerve paresis. Many workgroups cited above are meanwhile exclusively working on this topic. The workgroup around Zealear succeeded already in 1996 in temporarily electrically stimulating the human vocalis muscle. Consequently, a fully implantable system (the Medtronic ITREL II System®, approved for the stimulation of the spinal cord in chronic pain conditions) was tested in 7 patients. A functionally sufficient opening of the hemilarynx could be reached in 4 patients. Stimulation occurred in a fixed rhythm without sensor-driven triggering. Partly not only the muscle but also neighboring nerves and muscles were stimulated. This led to undesired co-movement of muscles. The electrodes corroded at the anode. This led to functional failure in two patients. Only 2-channel systems could be used. This led to limitations in cases of electrode failure or during functional fitting. Excessively high stimulation amplitudes (>8.5 mA) caused pain.

Werner Lindenthaler, worked on further developing the laryngeal pacemaker. See, e.g., U.S. Pat. No. 7,069,082, which is incorporated by reference herein, in its entirety. Using highly flexible multi-electrodes and minimally invasive application techniques, surgical trauma for the surrounding muscles was considerably reduced. See, e.g., U.S. Patent Application Publication Nos. 2008/0091247, 2008/0071230, 2008/0071245, 2008/0071244, 2008/0071231. Focusing on autoparalytic reinnervated laryngeal muscles and multi-channel electrodes enabled stimulation of the desired glottis movement with considerably lower current intensities and measurement of the induced movement of the glottis with the Endoscan system. Even after long-term paresis, ankylosis of the joint, which would impede glottis stimulation, did not occur. Synchronization of glottis stimulation with respiration, swallowing and vocalization, which had not been considered by Zealear and colleagues, was integrated into the concept of the laryngeal pacemaker and EMG signal analyses were performed.

The most extensive experience in the area of electrostimulation in ENT medicine exists for the cochlear implant. More than 60,000 patients worldwide have received a cochlear implant. Cochlear implants are the most highly developed electrostimulation implants. They stimulate at 12-24 channels (cardiac pacemakers at 1, pain pacemakers at 4-8) with up to 20,000 pulses per second (cardiac pacemakers with 1, pain pacemakers with up to 190) per channel, up to a maximum of 50,000 Hz. They process incoming signals in various amplitude ranges and frequencies up to 20,000 Hz (at present only cardiac pacemakers with EMG signal recording and foot-drop implants with external heel switches are approved marketed systems with sensors). Cochlear implants are meanwhile also able to measure evoked potentials in the middle ear. The electrodes are thinner and more flexible than cardiac pacemaker electrodes, pain, Parkinson, tremor etc., pacemaker electrodes, although they have considerably more recording and stimulation contacts. Due to the high stimulation rate, cardiac pacemaker batteries would last only about 17 days, therefore cochlear implants are still inductively coupled systems, i.e., energy and signals are transmitted through the skin to the implanted stimulator via high frequency.

Functional electrostimulation of other parts of the body has made considerable progress over the last 40 years. FDA-approved neuroprostheses to control the paralyzed hand, to control intestinal and bladder function or respiration by triggering the diaphragm are available in the USA. The stimulation systems are either placed on the affected body surface (e.g. Handmaster®, Ness Ltd, Israel or BioNess Inc, Spain) or implanted (e.g. FESMate®, NEC, Japan or Freehand®, CWRU, USA; for the bladder: Finetech-Brindley Bladder System, United Kingdom; or the diaphragm: Avery Mark IV, Avery, USA and MedImplant, Austria). While first-generation devices worked exclusively via external triggers, new devices use sensors to detect muscle or joint position or EMG signals of neighboring intact muscle for improved impulse control. These developments led to improved electrodes (reduced risk of breakage, multi-channel systems) and improved stimulation units (miniaturization, implantability).

Beside intramuscular electrodes and implantable muscle surface electrodes (epimysial electrodes), extraneural electrodes such as cuff electrodes, epineural and interfascicular electrodes have also been developed. These electrodes have the advantage of a more selective stimulation of the enclosed nerve at the price of more invasive implantation.

Recently, it has been shown that it is possible to activate a denervated muscle via remote control. For example, in rats the denervated gastrocnemius muscle was successfully contracted via an EMG trigger from the same muscle of a second, healthy animal using a remote radiofrequency system.

FIGS. 1A and 1B show diagrams of the normal somatotopic organization of facial innervation and the organization after lesion of the facial nerve, respectively. As shown in FIG. 1A, normally exactly one axon 10 projects to one end-plate on the muscle fiber 12. Each of the different muscle groups 14 of the face is activated by the motor neuron pool of a subnucleus of the nucleus. As shown in FIG. 1B, despite transsection and optimal reconstruction of the facial nerve, the regenerating axons 10 may sprout collaterally at the site of the lesion. The axons 10 sprout purely accidentally to any muscle fibers 12. Somatotopic order is lost. The clinical result is synkinesis.

Figure 2B:
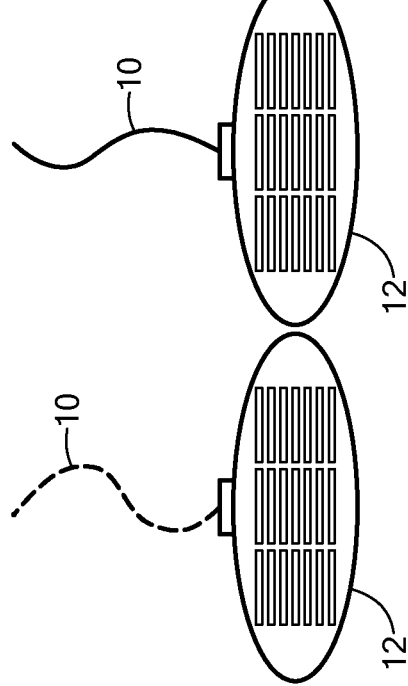

FIGS. 2A and 2B show diagrams of a normal end-plate region on the muscle fiber 12 and end-plate regions activated by several axons 10 due to terminal sprouting, respectively. As shown in FIG. 2A, normally exactly one axon 10 projects to one end-plate on the muscle fiber 12. After transsection and surgical reconstruction, however, terminal sprouting may occur (such as shown in FIG. 2B) in addition to collateral sprouting. In this case, individual end-plates may be activated by several axons 10. Thus, in subjects with these kinds of problems, activating a desired facial muscle may entail considerable challenges since stimulating a nerve branch on the damaged side of the subject's face may not activate the corresponding facial muscle, but an entirely different, unpredictable facial muscle or muscles.

Figure 3:
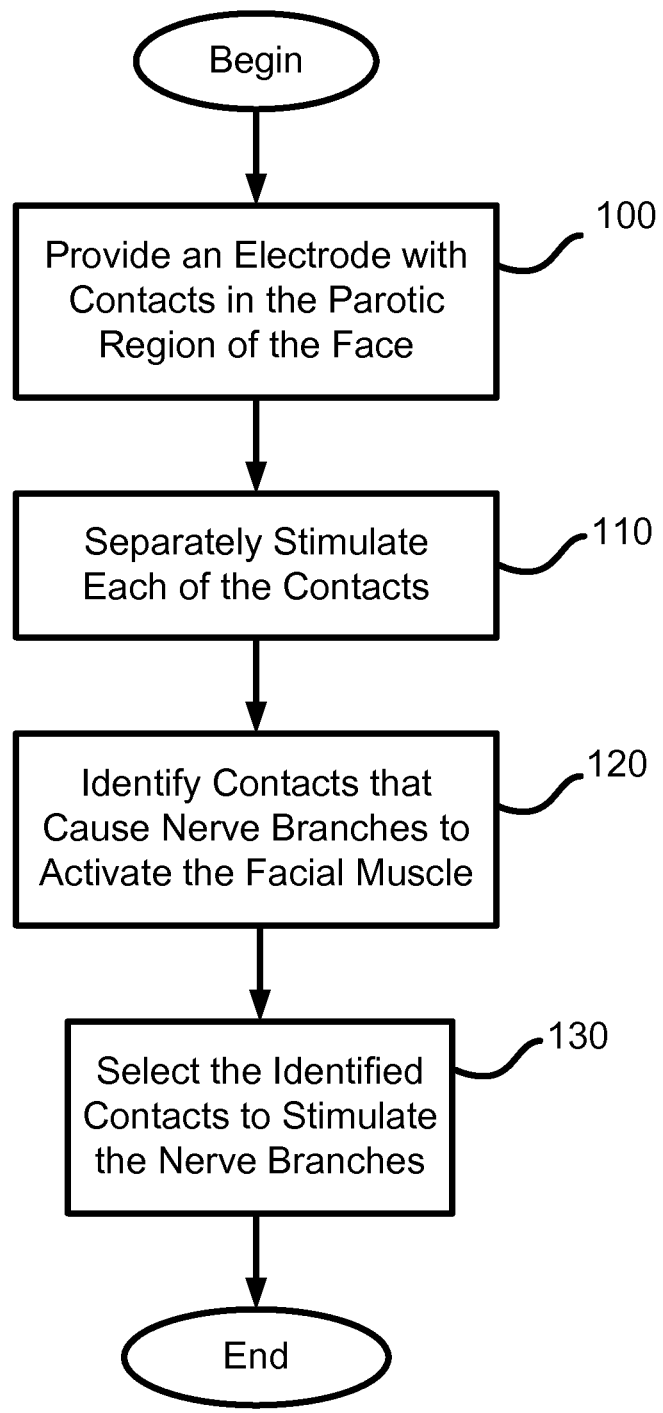
FIG. 3 shows a process of activating facial nerves according to embodiments of the present invention.
Figure 4:
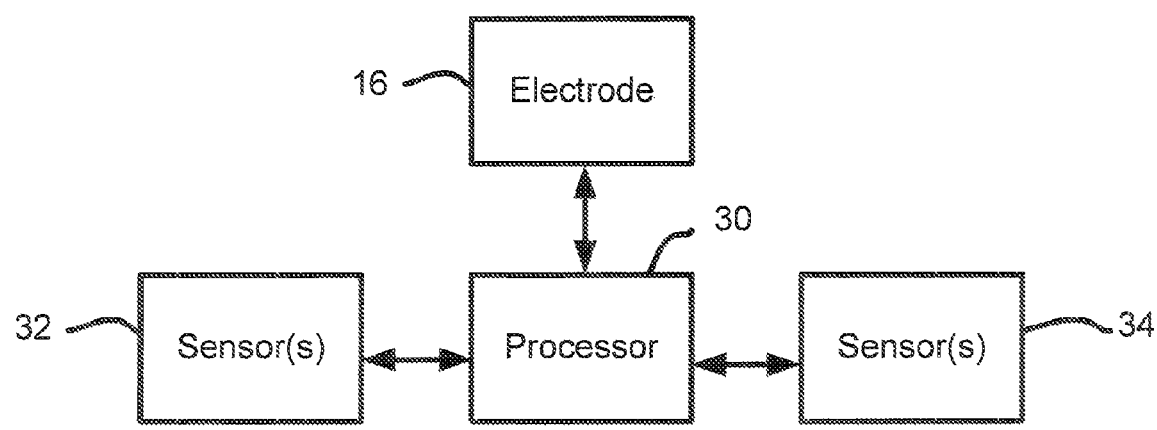
FIG. 4 shows a system for activating facial nerves according to embodiments of the present invention.
Figure 5:
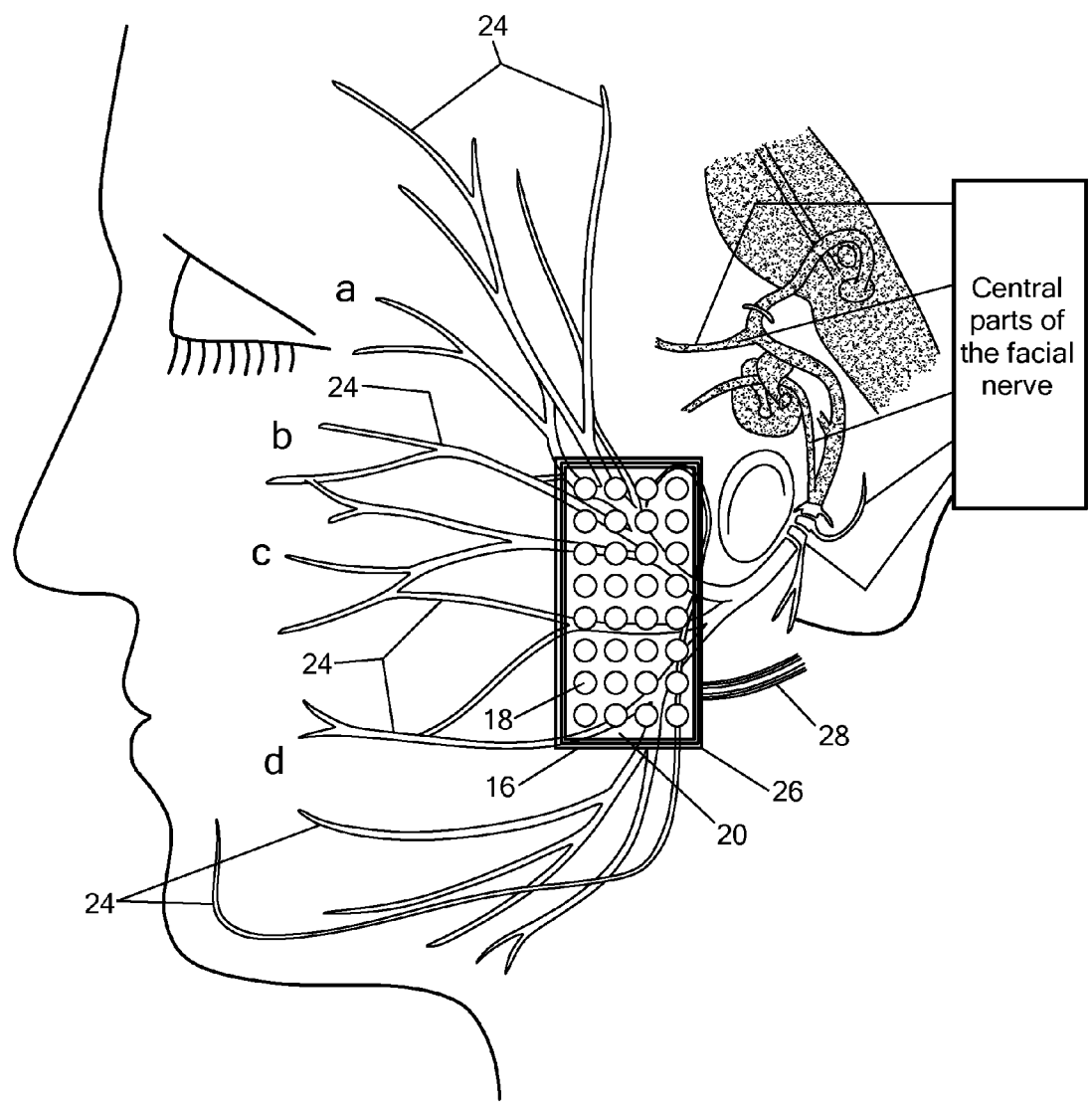
FIG. 5 shows an array electrode in the parotic region in relation to the branches of the facial nerve according to embodiments of the present invention.
Figure 6:
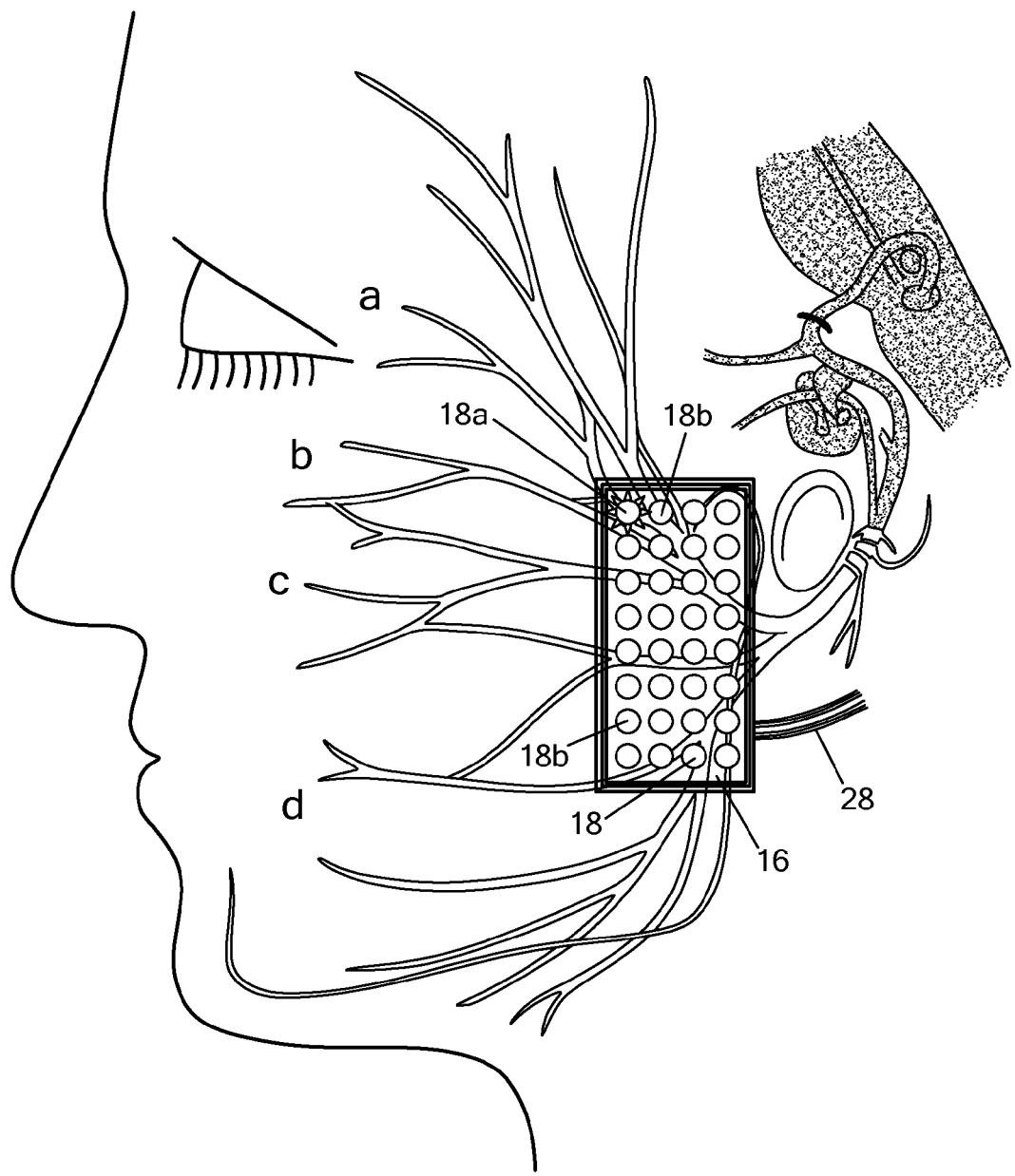
FIG. 6 shows one contact stimulating a nerve branch according to embodiments of the present invention.
Figure 7:
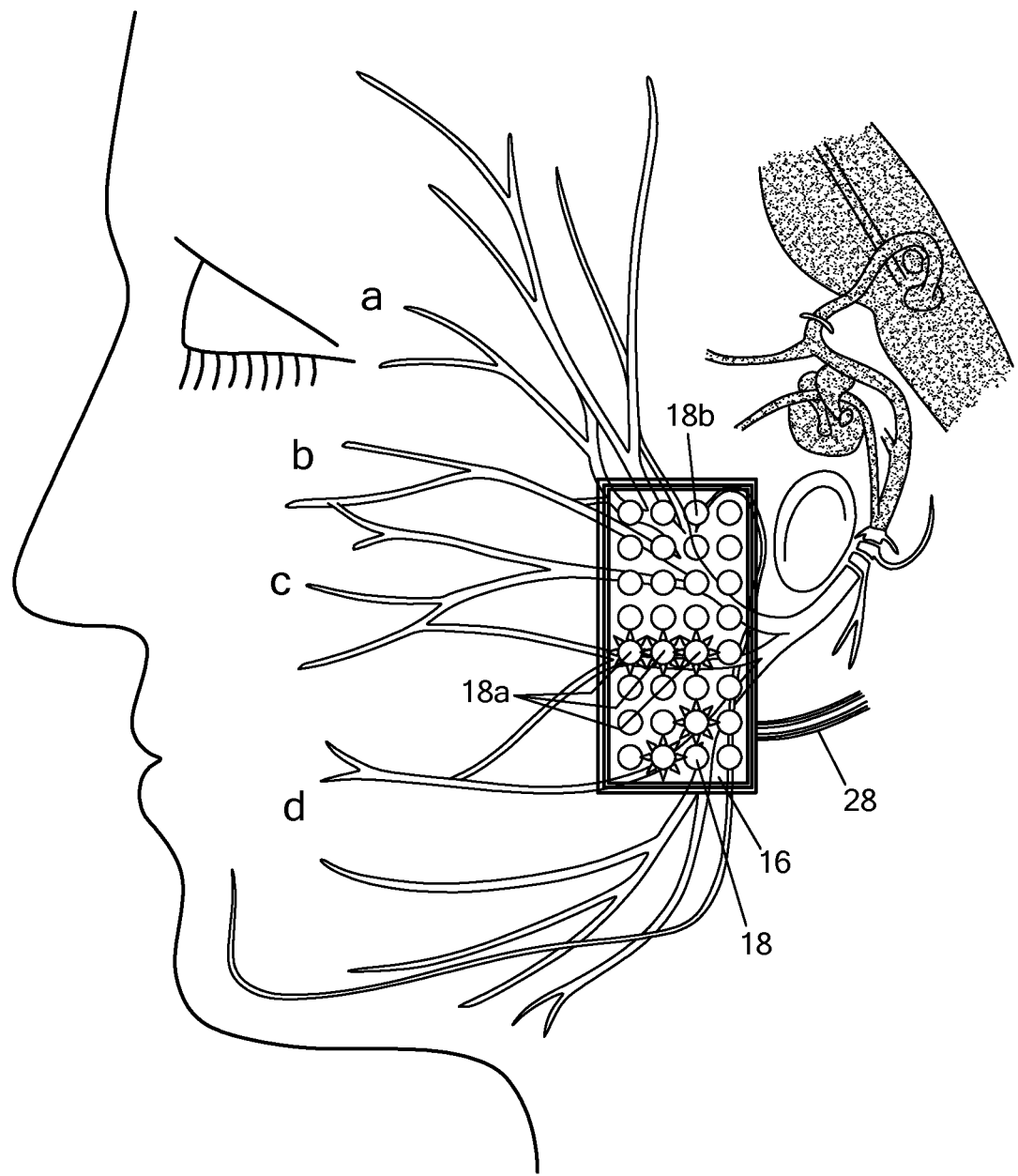
FIG. 7 shows several contacts simultaneously stimulating nerve branches according to embodiments of the present invention.
Figure 9:
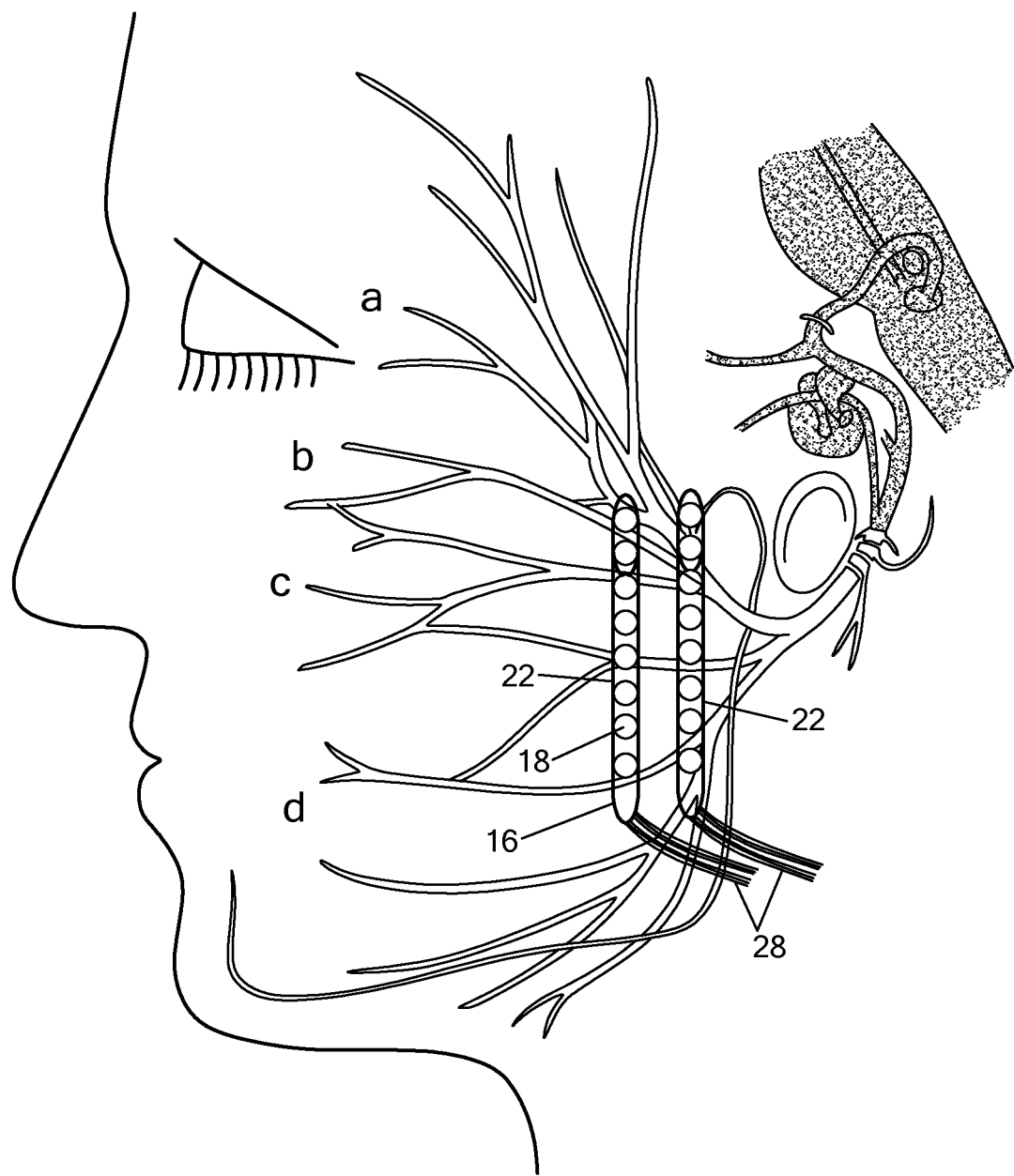
FIG. 9 shows two rod electrodes in the parotic region of the facial nerve according to embodiments of the present invention.
Figure 10:
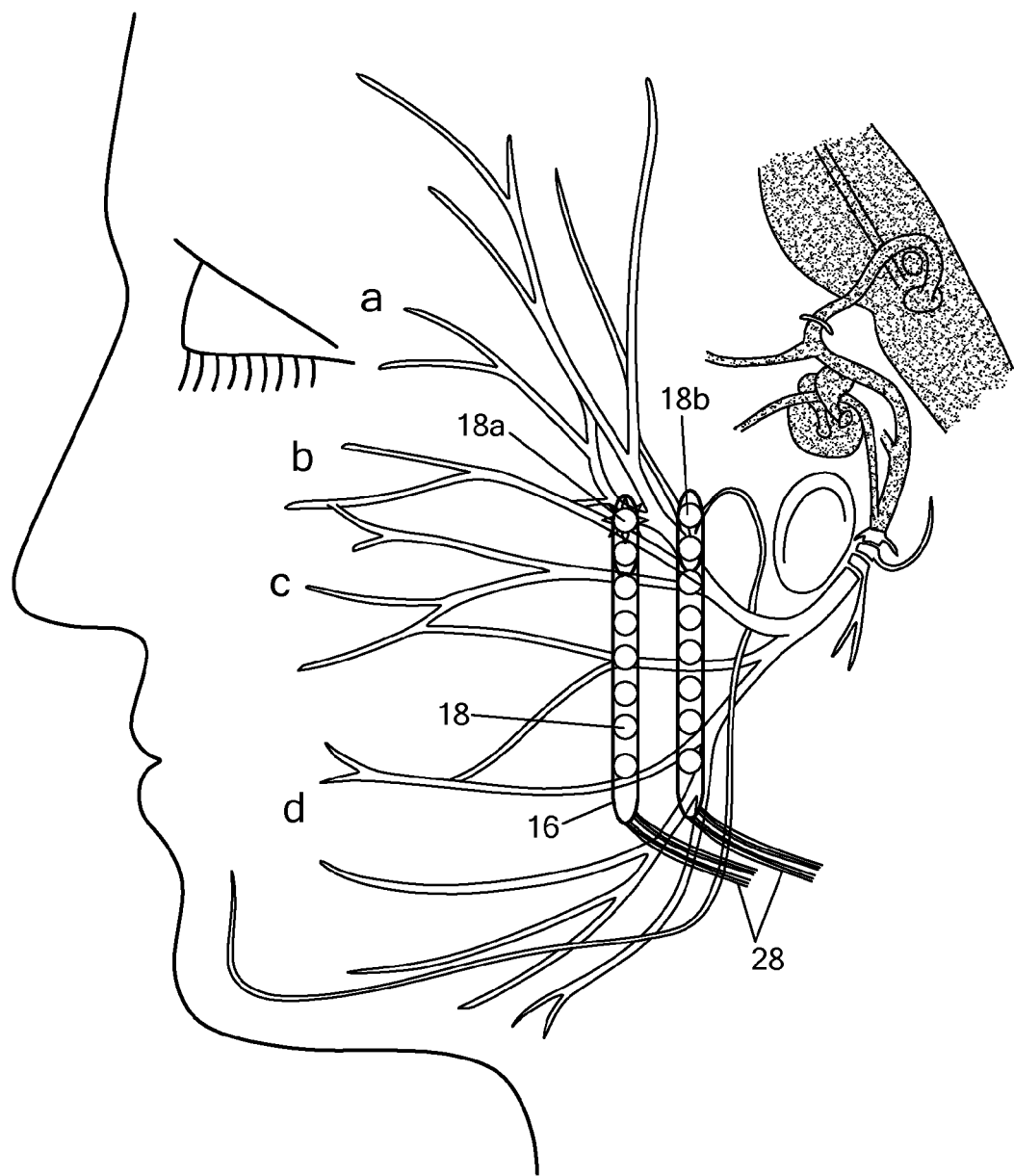
FIG. 10 shows one contact stimulating a nerve branch according to embodiments of the present invention.
Figure 11:
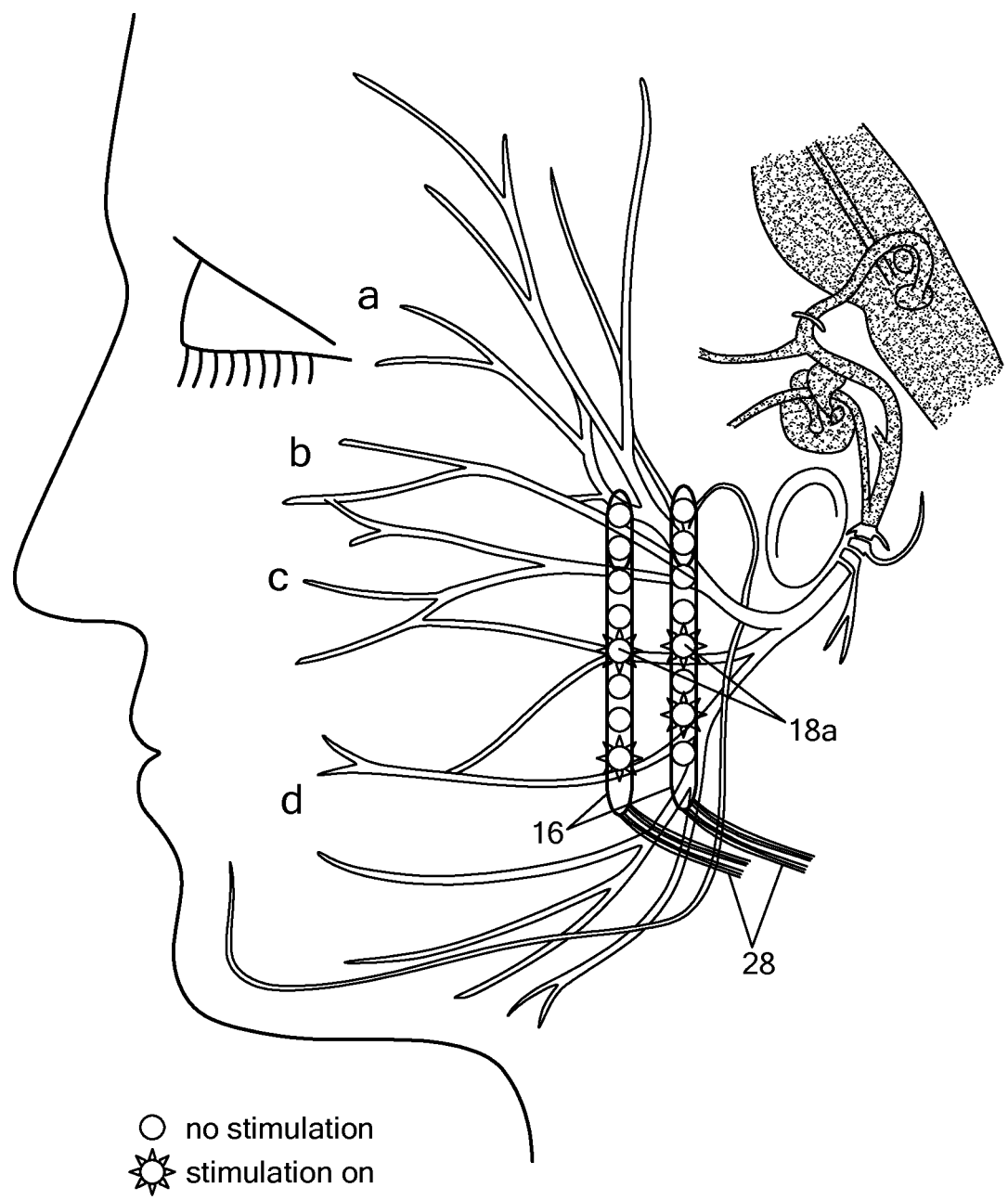
FIG. 11 shows several contacts simultaneously stimulating nerve branches according to embodiments of the present invention.

Various embodiments of the present invention provide a system and method of activating the desired facial muscle by stimulating the appropriate facial nerves in subjects with synkinetic reinnervated muscles. FIG. 3 shows a process of stimulating facial nerves and FIG. 4 shows a system for stimulating facial nerves according to embodiments of the present invention. The process begins at step 100, in which an electrode 16 is provided in the parotic region of the subject's face, such as shown in FIG. 5. The electrode 16 has a plurality of contacts 18, which may be configured in rows and columns (e.g., an array electrode 20 such as shown in FIGS. 5-7), or configured in one or more rows (e.g., one or more rod electrodes 22 such as shown in FIGS. 9-11). The contacts 18 may be used to stimulate nerve branches 24 or to record nerve impulses or potentials from the nerve branches 24. The electrode 16 may have an insulating electrode pad 26 surrounding the contacts 18 and an electrode lead 28 electrically connecting the electrode 16 to a processor 30 for controlling the stimulation and/or recording of the electrode 16. The processor 30 may also provide signal processing capabilities to the stimulation and/or recording signal information.

The electrode 16 is implanted in the parotic region within an operable distance of stimulating the branches 24 of the distal part of the facial nerve. The benefit of placing the electrode 16 in this region is that the facial nerve is already split up into separate nerve branches 24, allowing different regions (e.g., designated a, b, c, and d in FIGS. 5-7 and 9-11) and functions of the face to be innervated separately. For example, two functions of the facial nerve may include closing the eyelids through the orbicularis oculi muscle (MOC) and pursing the lips through the orbicularis oris muscle (MOR). Other facial muscles may also be innervated, such as the occipitofrontalis muscle, the procerus muscle, the nasalis muscle, the depressor septi nasi muscle, the corrugator supercilii muscle, the depressor supercilii muscle, the auricular muscles (anterior, superior, posterior), the depressor anguli oris muscle, the risorius muscle, the zygomaticus major muscle, the zygomaticus minor muscle, the levator labii superioris muscle, the levator labii superioris alaeque nasi muscle, the depressor labii inferioris muscle, the levator anguli oris muscle, the buccinator muscle, and/or the mentalis muscle. The electrode 16 may be implanted above the facial nerve between the nerve and the skin or below the facial nerve. The various contacts 18 may provide the stimulation or recording (or no stimulation or no recording) sequentially or simultaneously, in a prescribed manner as discussed in more detail below.

In step 110, each of the contacts 18 in the electrode 16 is stimulated separately in order to determine which nerve branches 24 activate which facial muscles. The movement of the various facial muscles may be measured by sensors 32 placed on the skin or implanted under the skin. The sensors 32 may be electromyographic (EMG) sensors, acceleration sensors, or other sensors that may effectively measure muscle movement as is well known to those skilled in the art. The sensors 32 are in communication with the processor 30 so that the contact stimulation information is correlated with the measured muscle movement information in order to determine which contact(s) 18 ultimately activated which facial muscle(s). The contacts 18 may be stimulated in a sequential manner (e.g., the first contact in the first row, first column, and then the second contact in the first row, second column, etc.) or in any order or pattern which would provide the desired information so long as one contact 18 is stimulated at a time. FIG. 6 shows one contact being stimulated (e.g., a star pattern denoting a stimulated contact 18a), while the remaining contacts are not stimulated (e.g., a plain circle denoting a contact 18b with no stimulation).

This initial assessment is especially important in subjects with synkinetic reinnervated muscles. For example, in a subject with normal somatotopic organization of facial innervation, nerve branch(es) for the eye would activate facial muscle(s) for the eye, and nerve branch(es) for the mouth would activate facial muscle(s) for the mouth, etc. However, in subject's with synkinetic reinnervated muscles, nerve branch(es) for the eye might activate other facial muscle(s) (e.g., facial muscles for the mouth or facial muscles for the mouth and the eye). Thus, by testing via stimulating each contact 18 of the electrode 16 separately, one or more contacts 18 are identified (in step 120) which stimulate nerve branches activating a particular facial muscle, e.g., muscle fibers responsible for closing the eye. If co-activation of other nerve branches happens at an unacceptable level, then one or more contacts 18 may even be used to block the other nerve branches. For example, if one contact stimulates nerve branch a+b, and another contact stimulates branch b, than a distal blocking stimulation of branch b combined with a proximal stimulation of branch a+b may selectively stimulate just branch a. The nerve blocking may be accomplished in a number of ways, such as nerve collision blocking, anodal blocking, high frequency blocking, etc.

In step 130, the identified contacts 18 are selected to stimulate the appropriate nerve branch(es) in order to activate a desired facial muscle. The processor 30 may determine which nerve branch(es) are the appropriate ones based on the measured muscle movement information. The processor 30 may then select and stimulate the identified contacts 18. As shown in FIG. 7, one or more contacts 18a may be stimulated simultaneously in order to activate one facial muscle. Two or more sets of contacts 18a may also be stimulated together to activate more than one facial muscle. For example, if one or more contacts are identified to activate a first facial muscle and one or more contacts are identified to activate a second facial muscle, then the first and second set of contacts may be selected at the same time to activate both facial muscles. The two sets of contacts may have some contacts in common, may be completely different contacts, or be the same contacts, depending on the subject's initial assessment.

In certain situations, such as in subjects with facial palsy, the processor 30 may continuously stimulate the identified contacts 18 with a fixed stimulation protocol without further sensor input, e.g., trigger signals from a healthy side of the face. This continuous stimulation may allow the nerve function to maintain or recover the resting tone of a hemiparalyzed face, since the asymmetry of the face at rest is typically the most striking stigma attracting the interest of other people.

Figure 8B:
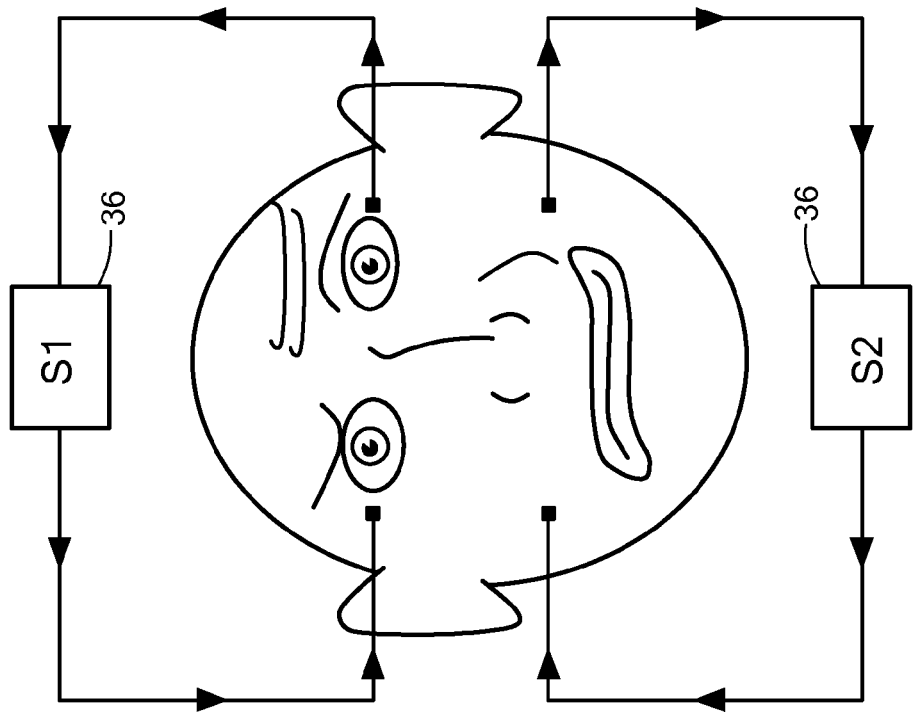
FIGS. 8A and 8B show diagrams of a unilaterally paralyzed face having a damaged right side and a healthy left side.
Figure 8A:
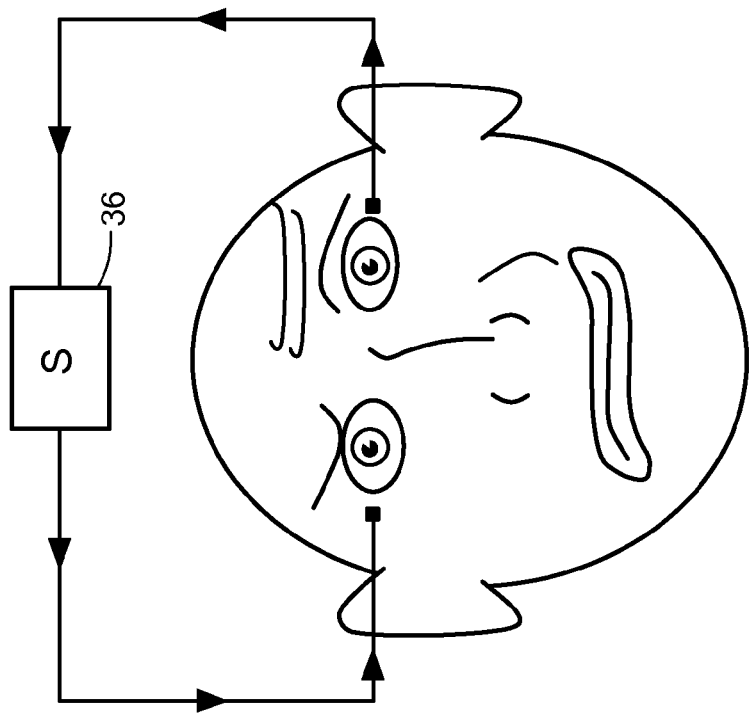

The initial assessment from the damaged side of the subject's face may be used in conjunction with facial movement information from the healthy side of the face. The initial assessment would ensure that the movement sensed on the healthy side triggers the appropriate muscles on the damaged side. For example, FIGS. 8A and 8B show diagrams of two unilaterally paralyzed faces, both having a damaged right side and a healthy left side. In FIG. 8A, a system of closing the eyelids through the MOC is shown and in FIG. 8B a system of closing the eyelids through the MOC and pursing the lips through the MOR is shown. After the initial assessment is determined, the facial movement on the healthy side of the face may be measured or recorded using one or more sensors 34. As shown in FIG. 8A, the facial movement information may, optionally, undergo amplification and/or modulation of the signal in a stimulation unit 36 (S), which may be in communication with the processor 30. The processor 30 may record or determine which muscles were moved on the healthy side of the face, determine which contact(s) 18 to select on the damaged side of the face in order to stimulate the appropriate nerve branches, and then select those contact(s) 18.

For example, the initial assessment may determine that the nerve branch(es) for the eye may actually activate the facial muscle(s) for the mouth, rather than the normal corresponding facial muscle(s) for the eye, and the nerve branch(es) for the mouth may activate the facial muscle(s) for the eye. When the sensors 34 measure that the facial muscle(s) for the eye have moved on the healthy side of the face, the processor 30 selects the contacts 18 that stimulate the nerve branch(es) for the mouth on the damaged side, which in turn activate the facial muscle(s) for the eye. Previously, in the prior art, the movement on the healthy side typically just triggers the same corresponding muscle on the damaged side which, in this example, would have moved the mouth muscles rather than the desired eye muscles on the damaged side of the face. After the initial assessment is determined, the facial movement on the damaged side of the face may alternatively be measured or recorded using one or more of the electrode contacts 18. The facial movement information may, optionally, undergo amplification and/or modulation of the signal in a stimulation unit 36 (S), which may be in communication with the processor 30. The processor 30 may record or determine which muscles should have been moved on the damaged side via recording the appropriate misdirected nerve branch signal of the face, determine which contact(s) 18 to select on the damaged side of the face in order to stimulate the appropriate misdirected nerve branch(es), and then select those contact(s) 18. This means contact 18a in FIG. 6 is measuring or recording information from a misdirected nerve fiber which would on the healthy side carry information for activation of a muscle innervated by nerve branch c. The facial movement information may, optionally, undergo amplification and/or modulation of the signal in a stimulation unit 36 (S), which may be in communication with the processor 30. The processor 30 may determine which muscles should have been moved on the damaged side and determine which contact(s) 18 to select on the damaged side of the face in order to stimulate the appropriate misdirected nerve branch(es), and then select those contact(s) 18a in FIG. 7.

As shown in FIG. 8B, the facial movement information from the healthy side of the face may be provided for more than one muscle system using additional sensors 34. In FIG. 8B, two separate stimulation units 36 (S1, S2) may, optionally, be used to amplify and/or modify the signals measured by the sensors 34. Although FIGS. 8A and 8B show one and two muscle systems, respectively, more than two muscle systems, or other muscle systems than those shown, may also be used. Similarly, although one or two stimulation units are shown, no stimulation unit or more than two stimulation units may also be used, or one stimulation unit may be used for two or more muscle systems.

An array electrode 20 has been shown and discussed in FIGS. 5-7, but other various shapes for the electrode 16 may also be used. For example, FIGS. 9-11 show a rod electrode implanted in the parotic region according to other embodiments of the present invention. As shown, two rod electrodes 22 with contacts 18 in a row may be implanted in the subject, although one rod electrode or more than two rod electrodes may also be used. The two rod electrodes are shown in a parallel orientation, but other configurations for two or more rod electrodes may be used which give good results for stimulation.

Some embodiments of the processor 30 may be implemented as hardware, software (e.g., a computer program product), or a combination of both software and hardware. For example, embodiments may be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions may embody all or part of the functionality previously described herein with respect to the processor. Those skilled in the art should appreciate that such computer instructions may be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

Although the above discussion discloses various exemplary embodiments of the invention, it should be apparent that those skilled in the art can make various modifications that will achieve some of the advantages of the invention without departing from the true scope of the invention.

What is claimed is:

1. A method of stimulating facial nerves in a subject with synkinetic reinnervated muscles, the method comprising:
providing an electrode in a parotid region of the subject's face, the electrode having a plurality of contacts;
stimulating one or more facial nerve branches by stimulating each of the plurality of contacts separately in order to determine which nerve branch activates which facial muscle in the subject with synkinetic reinnervated muscles;
identifying one or more contacts from the plurality of contacts that cause the one or more nerve branches to activate a desired facial muscle; and
selecting the identified contacts to stimulate the one or more nerve branches.

2. The method of claim 1, wherein the electrode is an array electrode.

3. The method of claim 1, wherein the electrode is a rod electrode.

4. The method of claim 1, wherein the parotid region includes nerve branches that activate facial muscles that include a orbicularis oculi muscle, a orbicularis oris muscle, a occipitofrontalis muscle, a procerus muscle, a nasalis muscle, a depressor septi nasi muscle, a corrugator supercilii muscle, a depressor supercilii muscle, a auricular muscle, a depressor anguli oris muscle, a risorius muscle, a zygomaticus major muscle, a zygomaticus minor muscle, a levator labii superioris muscle, a levator labii superioris alaeque nasi muscle, a depressor labii inferioris muscle, a levator anguli oris muscle, a buccinator muscle, and a mentalis muscle.

5. The method of claim 1, wherein providing the electrode includes implanting the electrode within an operable distance of the one or more nerve branches.

6. The method of claim 1, further comprising selecting one or more contacts to stimulate nerve branches in order to block activation of other facial muscles.

7. The method of claim 1, wherein stimulation of the one or more nerve branches is triggered based on a sensed signal.

8. The method of claim 7, wherein the sensed signal is recorded from a recording electrode in the parotid region of the subject's damaged side of the face, the recording electrode having a plurality of contacts.

9. The method of claim 7, wherein the sensed signal is recorded from a recording electrode in the parotid region of the subject's healthy side of the face, the recording electrode having a plurality of contacts.

10. The method of claim 7, wherein the sensed signal is recorded from sensors placed on or under the subject's skin.

11. The method of claim 1, wherein identifying one or more contacts includes one or more first contacts that cause the activation of a first facial muscle and one or more second contacts that cause the activation of a second facial muscle; and
selecting the identified contacts includes selecting the identified first and second contacts.

12. The method of claim 1, wherein the identified contacts continuously stimulate the one or more nerve branches.

13. The method of claim 12, wherein the electrode is an array electrode.

14. The method of claim 12, wherein the electrode is a rod electrode.

15. The method of claim 12, wherein providing the electrode includes implanting the electrode within an operable distance of the one or more nerve branches.

16. The method of claim 12, wherein stimulation of the one or more nerve branches is triggered based on a sensed signal.

17. The method of claim 16, wherein the sensed signal is recorded from sensors placed on or under the subject's skin.

18. The method of claim 12, wherein identifying one or more contacts includes one or more first contacts that cause the activation of a first facial muscle and one or more second contacts that cause the activation of a second facial muscle; and selecting the identified contacts includes selecting the identified first and second contacts.

\* \* \* \* \*